United States Patent [19]

Martin

[11] Patent Number: 4,781,195

[45] Date of Patent: Nov. 1, 1988

[54] BLOOD MONITORING APPARATUS AND METHODS WITH AMPLIFIER INPUT DARK CURRENT CORRECTION

[75] Inventor: Alan D. Martin, Boulder, Colo.

[73] Assignee: The BOC Group, Inc., Montvale, N.J.

[21] Appl. No.: 127,742

[22] Filed: Dec. 2, 1987

[51] Int. Cl.⁴ .................. A61B 5/00; G01N 33/49
[52] U.S. Cl. ................................. 128/633; 356/41
[58] Field of Search ............... 128/633, 664, 665, 667; 356/41

[56] References Cited

U.S. PATENT DOCUMENTS

| 4,407,290 | 10/1983 | Wilber | 128/633 |
| 4,586,513 | 5/1986 | Hamaguri | 128/633 |
| 4,653,498 | 3/1987 | New | 128/633 |

Primary Examiner—Alan Cohan
Attorney, Agent, or Firm—Larry R. Cassett; Roger M. Rathbun

[57] ABSTRACT

In photoelectric apparatus such as a pulse oximeter for monitoring a parameter of the blood in a living organism, a dark current correction signal is applied to the input at the preamplifier. The correction signal is substantially equal in magnitude but opposite in sense to the photodetector output during dark intervals when the illumination means of the apparatus is disabled. Because dark current correction is accomplished at the input of the preamplifier, the preamplifier has substantially increased resistance to overloading caused by ambient light and hence may have higher gain.

14 Claims, 2 Drawing Sheets

BLOOD MONITORING APPARATUS AND METHODS WITH AMPLIFIER INPUT DARK CURRENT CORRECTION

BACKGROUND OF THE INVENTION

The present invention relates to apparatus and methods for monitoring a parameter in the blood of a living organism.

Certain constituents in the blood affect the absorption of light at various wavelengths by the blood. For example, oxygen in the blood binds to hemoglobin to form oxyhemoglobin. Oxyhemoglobin absorbs light more strongly in the infrared region than in the red region, whereas hemoglobin exhibits the reverse behavior. Therefore, highly oxygenated blood with a high concentration of oxyhemoglobin and a low concentration of hemoglobin will tend to have a high ratio of optical transmissivity in the red region to optical transmissivity in the infrared region. The ratio of transmissivities of the blood at red and infrared wavelengths can be employed as a measure of oxygen saturation.

This principle has been used heretofore in oximeters for monitoring oxygen saturation of the blood in the body of a living organism as, for example, in patients undergoing surgery. As disclosed in U.S. Pat. No. 4,407,290, oximeters for this purpose may include red light and infrared light emitting diodes together with a photodetector. The diodes and photodetector typically are incorporated in a probe arranged to fit on a body structure such as an earlobe or a fingertip, so that light from the diodes is transmitted through the body structure to the photodetector. The infrared and red light emitting diodes are switched on and off in alternating sequence at a switching frequency far greater than the pulse frequency. The signal produced by the photodetector includes alternating portions representing red and infrared light passing through the body structure. These alternating portions are amplified and then segregated by sampling devices operating in synchronism with the red/infrared switching, so as to provide separate signals on separate channels representing the red and infrared light transmission of the body structure. After low-pass filtering to remove signal components at or above the switching frequency, each of the separate signals represents a plot of optical transmissivity of the body structure at a particular wavelength versus time.

Because the volume of blood in the body structure varies with the pulsatile flow of blood in the body, each such signal includes an AC component caused only by optical absorption by the blood and varying at the pulse frequency or heart rate of the organism. Each such signal also includes an invariant or DC component related to other absorption, such as absorption by tissues other than blood in the body structure. According to well known mathematical formulae, set forth in said U.S. Pat. No. 4,407,290, the oxygen saturation in the blood can be derived from the magnitudes of the AC and DC components of these signals.

As also set forth in the '290 patent, the same general arrangement can be employed to monitor constituents of the blood other than oxygen such as carbon dioxide, carbon monoxide (as carboxyhemoglobin) and/or blood glucose, provided that the other constituents have some effect on the optical properties of the blood. Also, information concerning the pulse of the patient can be obtained from the AC signal components. As used in this disclosure, the term "parameter of the blood" includes the level of any constitutent and also includes parameters related to the pulse, such as the pulse rate and the occurrence or non-occurrence of pulses.

Measurement apparatus and methods of this type have been widely adopted in the medical profession. However, such apparatus and methods have been subject to interference from ambient light falling on the photodetector. The apparatus has been provided with circuits for cancelling components caused by ambient light. These circuits operate by obtaining a "dark current" signal representing the amplified photodetector signal during intervals when both of the light emitting diodes are off and hence all of the light falling on the photodetector represents ambient light. The dark current signal value is used to cancel the ambient light component in the amplified signals representing infrared and red light.

This approach provides only a partial solution to the ambient light interference problem. The ambient light impinging upon the photodetector may be far stronger than the light transmitted through the patient's body. Accordingly, components of the photodetector signal caused by ambient light may be far larger than the useful photodetector signal components representing light transmitted through the body structure. The ambient light components can overload the first amplifier in the system, commonly referred to as the preamplifier. To avoid such overloading, the gain of the preamplifier has been limited heretofore. The limited gain available in the preamplifier may result in a loss of sensitivity in the instrument as a whole and may require greater gain in subsequent stages used to amplify various portions of the signal.

The conventional preamplifier utilized heretofore incorporates an operational amplifier having inverting and non-inverting input nodes and an output node. The non-inverting input node may be grounded. The photodetector signal, typically a current from a photodiode operating in a photoamperic mode, is connected to the inverting input node of the operational amplifier. A feedback resistor is connected between the inverting input node and the output node. In this "transresistance" amplification arrangement, the operational amplifier creates a voltage at the output node opposite in sense to the voltage at the inverting input node. The opposite sense voltage causes a current flow through the feedback resistor opposite in sense to the current flow applied by the photodetector. The preamplifier comes to equilibrium when the current flow out of the inverting input node through the feedback resistor exactly balances the current flow into the inverting input node through the photodetector. The gain or ratio of output node voltage to incoming signal is proportional to the value of the feedback resistor. The greater the value of the feedback resistor, the greater the opposite sense voltage at the output node must be to achieve balance.

In the typical dark current cancellation circuitry utilized heretofore, the output node of the preamplifier is connected to a first side of a capacitor, whereas the second side of the capacitor is connected to the downstream signal processing equipment. A controllable switch is connected between the second side of the capacitor and ground. The switch is closed only when the light emitting diodes are off, i.e., only during dark intervals. During each dark interval the preamplifier output node voltage represents only the component caused by the ambient light. With the second side of the capacitor grounded, the charge on the capacitor accumulates until the voltage across the capacitor is equal to this voltage. When the dark interval ends, the switch is opened, leaving the charged capacitor connected between the amplifier output node and the downstream signal processing apparatus. Therefore, the voltage applied to the signal processing apparatus will be the preamplifier output voltage less the voltage across the capacitor, i.e., the preamplifier output voltage less the voltage component caused by ambient light. So long as changes in ambient light levels between successive dark intervals are relatively small, this arrangement should theoretically provide good cancellation of the signal components caused by the ambient light.

However, the dark current cancellation afforded in this arrangement does not alleviate the problem of preamplifier overloading. Thus, the operational amplifier must still provide sufficient voltage at the output node so that the current through the feedback resistor completely balances both the useful and ambient-light components of the signal applied to the input node. The value of the feedback resistor, and hence the gain of the preamplifier must be limited to avoid exceeding the capacity of the operational amplifier. Additionally, the operational amplifier is connected directly to a significant capacitive load. Depending upon the design of the particular operational amplifier, the capacitive load may induce instabilities in the operational amplifier.

Accordingly, there have been needs for further improvements in the blood parameter measuring apparatus, and specifically in the ambient light cancellation arrangements used therein.

SUMMARY OF THE INVENTION

One aspect of the present invention incorporates the realization that the problems caused by ambient light can be substantially alleviated by correcting for dark current upstream of the preamplifier or first amplification stage. In preferred apparatus and methods according to this aspect of the invention, a correction signal substantially equal in magnitude but opposite in sense to the component of the photodetector signal caused by ambient light is applied to the input node of the preamplifier. Because the correction signal is applied to the input node, it effectively counteracts the ambient light component in the photodetector signal before that component has any effect on the preamplifier. Therefore, the components in the photodetector signal caused by ambient light cannot cause overloading of the preamplifier. For the same reason, the gain of the preamplifier need not be limited to avoid such overloading. This aspect of the present invention thus provides improved apparatus and methods for monitoring a parameter of the blood in a body structure.

Apparatus according to this aspect of the present invention preferably includes photodetector means for detecting light and producing a photodetector output signal related to the amount of light impinging upon the photodetector means. The apparatus also preferably includes preamplification means having an input node for providing an amplified signal related to the signal applied to the input node. The input node is connected to the photodetector means for receipt of the photodetector output signal. Illumination means preferably are provided for emitting light and directing the emitted light through the body structure so that the emitted light transmitted through the body structure will impinge upon the photodetector means. Timing means are provided for periodically interrupting the operation of the illumination means to provide dark intervals. Thus, during each dark interval the photodetector output signal will be a dark interval photodetector output signal indicative of the ambient light impinging on the photodetector means. Correction means are provided for applying to the input node of the preamplification means a correction signal substantially equal in magnitude but opposite in sign to the dark interval photodetector output signal prevailing during the preceding dark interval. Thus, during the time periods between dark intervals, while the illumination means is operating, the net signal supplied to the input node will be the photodetector signal less the correction signal. In effect, the ambient light component is subtracted out of the photodetector signal before the photodetector signal ever passes into the input node of the preamplifier. As the input signal to the preamplifier means is already substantially corrected for the effect of ambient light on the photodetector means, the amplified signal from the preamplifier means will be substantially corrected for ambient light effects.

Preferably, the correction means includes means for determining the photodetector output signal prevailing during each dark interval by monitoring the amplified signal from the preamplification means. Thus, the correction means may include feedback loop means for applying a correction signal during each dark interval, adjusting the correction signal during the dark interval until the amplified signal goes to zero and then maintaining the correction signal at the value established by this adjustment until the next dark interval. Thus, the correction means may include means for integrating the amplified signal during each dark interval and means for providing the correction signal during periods between the dark intervals responsive to the integrated, amplified signal accumulated during the last previous dark interval. Typically, the photodetector means is arranged to provide the photodetector output signal as a photodetector current such that the magnitude of this current is directly related to the amount of light impinging on the photodetector means. The correction means may thus include means for applying the correction signal to the preamplifier input node as a current substantially equal but opposite in sense to the photodetector current prevailing during the last preceding dark interval.

The present invention also includes methods of monitoring a parameter of the blood in a living subject. Preferred methods according to this aspect of the invention include steps similar to the function discussed above in connection with the apparatus. In preferred methods according to this aspect of the invention, the photodetector output signal or current is determined during each dark interval and a corresponding but opposite correction signal or current is applied to the input node of the preamplifier means until the next succeeding dark interval. Methods according to this aspect of the invention afford advantages similar to those achieved with the apparatus.

These and other objects, features and advantages of the present invention will be more readily apparent from the detailed description of the preferred embodiments set forth below taken in conjunction with the accompanying drawings.

DETAILED DESCRIPTION OF THE PREFERRED EMBODIMENTS

Figure 1:
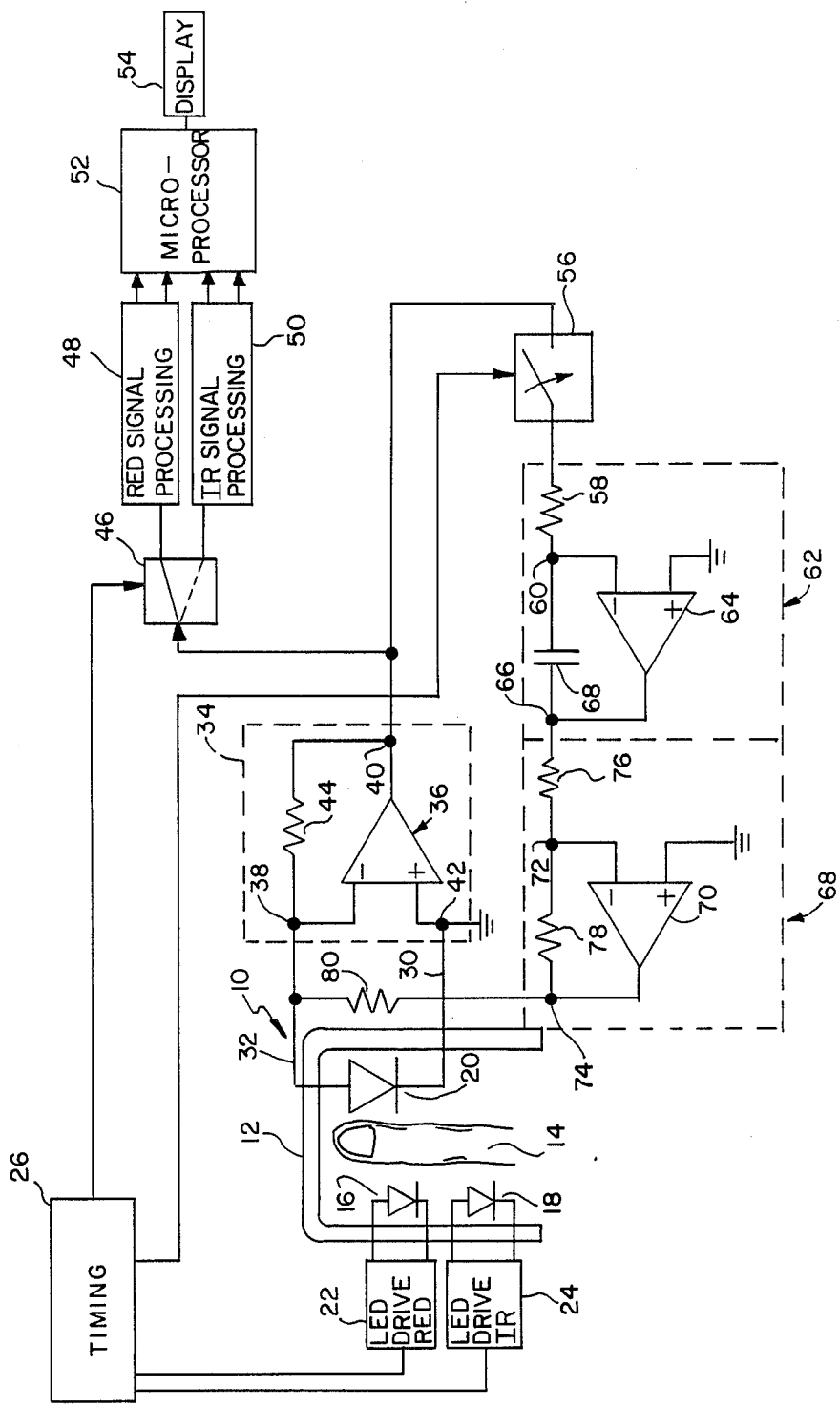
FIG. 1 is a schematic, partially block-form diagram of apparatus according to one embodiment of the invention.

Apparatus according to one embodiment of the present invention includes a probe 10 incorporating a clip 12 arranged to engage a body structure such as finger 14. The probe also includes a red light emitting diode 16 and an infrared light emitting diode 18 mounted to clip 12, together with a photodetector or photodiode 20 also mounted to clip 12. The light emitting diodes or "LED's" and photodiode are arranged so that light emitted by the LED's will pass through the finger 14 and impinge upon the photodiode. A red LED drive 22 and infrared or "IR" LED drive 24 are connected to LED's 16 and 18 respectively. A timing unit 26 is arranged to actuate LED drives 22 and 24, and hence LED's 16 and 18, according to a predetermined alternating sequence interspersed with dark intervals. During each such dark interval, the timing unit 26 deactivates the LED drives and hence deactivates both LED's. Thus, the LED drives and LED's provide alternating red and infrared illumination, whereas the timing unit periodically interrupts this illumination to provide the dark intervals.

Photodiode or photodetector 20 has a reference node 30 connected to ground and an output node 32. A front end amplifier or preamplification means 34 is also provided. Preamplification means 34 includes an operational amplifier 36 defining an inverting input node 38, an output node 40 and a non-inverting input node 42 connected to ground. Node 38 is an "inverting" node in the sense that amplifier 36 tends to produce a voltage at output node 40 opposite in sense to voltage at node 38. A feedback resistor 44 is connected between inverting node 38 and output node 40. photodetector output node 32 is connected to the inverting input node 38 of operational amplifier 36.

The output node 40 of the preamplifier is connected to a sampling switch 46, which in turn is connected to a red signal processing channel 48 and an IR signal processing channel 50. Sampling switch 46 is controlled by timing unit 26 so that switch 46 operates in synchronism with the predetermined sequence of red and infrared emission from LED's 16 and 18. Thus, switch 46 samples the amplifier output signal at preamplifier output node 40 and provides a sequence of samples to each signal processing channel. While LED 16 is providing red light, the amplified signal obtained from preamplifier 34 is routed through switch 46 to red signal processing channel 48. Conversely, when infrared light is being emitted by diode 18, the amplified signal is routed to IR signal processing channel 50. During dark intervals, while neither diode is operative, the amplified output signal is not routed to either signal processing channel.

Each of signal processing channels 48 and 50 may include generally conventional elements for converting the periodic signal samples supplied through switch 46 into a substantially continuous, smoothed signal, eliminating spurious components resulting from the switching process itself and determining the AC and DC components of the smoothed signal. For example, each signal processing channel may include a first low pass filter having its input connected to switch 46. The first low pass filter typically has a top cutoff frequency of about 10 Hz, and is arranged to attenuate signals above that frequency. The output of the first low pass filter is connected directly to a first analog to digital converter, and also to the input of a high pass filter. The high pass filter is arranged to attentuate signals below about 0.5 Hz. The output of the high pass filter may be connected to the input of an amplifier within the signal processing channel, and the output of this amplifier may be connected to a further low pass filter also having a top cutoff frequency of about 10 Hz. The output of this further low pass filter is connected to the input of a sample and hold unit, and the output of the sample and hold unit in turn is connected to a second analog to digital converter. A microprocessor 52 is connected to both signal processing channels 48 and 50, the microprocessor being arranged to receive digital values from the first and second analog to digital converter of each channel. The microprocessor is also connected to a display unit 54.

Output node 40 of preamplifier means 34 is also connected to the input side of an integrator switch 56. Switch 56 is controlled by timing unit 26. The output side of integrator switch 56 is connected through an integrator input resistor 58 to an input node 60 of an integrator 62. The integrator includes an integrator operational amplifier 64 having an inverting input connected to integrator input node 60, a non-inverting input node connected to ground and an output connected to the output node 66 of the integrator. The integrator also includes a capacitor 68 connected between integrator input node 60 and integrator output node 66. Integrator 62 is arranged to provide, at node 66, a voltage directly related to the integral of the voltage applied to node 60.

Inverter means 68 includes an operational amplifier 70 defining an inverting input node 72, a noninverting input node connected to ground and an output node 74. Inverter input node 72 is connected through an inverter input resistor 76 to the output node 66 of integrator 62, and an inverter feedback resistor 78 is connected between inverter input node 72 and inverter output node 74. Inverter output node 74 is connected through a proportioning resistor 80 to the input node 38 of preamplifier means 34.

In operation, timing unit 26 actuates LED drives 22 and 24 and LED's 16 and 18 alternately, and periodically interrupts operation of the LED's and LED drives to provide dark intervals during which neither LED is illuminated. During each such dark interval, timing unit 26 causes switch 56 to close thereby connecting preamplifier means output node 40 through resistor 58 to integrator input node 60. During a dark interval, only the ambient light impinges upon photodiode 20. As the current produced by photodiode 20 is directly related to the amount of light impinging on the photodiode, the current flowing out of the photodiode output node 32 at this time is directly related to the amount of ambient light. The current from the diode reaching preamplifier means input node 38 tends to cause operational amplifier 36 to swing the voltage at preamplifier output node 40 in the negative direction. This negative voltage is applied to the input node 60 of integrator 62, and hence causes integrator 62 to provide a positive voltage at integrator output node 66. This positive voltage at input node 66 increases in magnitude continually while the voltage at preamplifier output node 40 is negative with respect to ground.

Inverter means 68 provides a negative voltage with respect to ground at output node 74 responsive to the positive voltage at the integrator output node 66, the negative voltage at node 74 being directly proportional to the positive voltage at integrator output node 66. Thus, the negative voltage at node 74 will progressivly increase while the voltage at preamplifier output node 40 remains negative. There will be a progressively increasing current flow towards node 74 and hence away from preamplifier input node 38. This progressively increasing current flow tends to counteract the current flowing towards the preamplifier input node from the photodetector.

Stated another way, a correction current is applied through the circuit branch leading through resistor 80, and the direction of this correction current is opposite to the direction of the dark current from photodector 20. So long as the dark current from photodector 20 exceeds the correction current, the output of preamplification means 34 at node 40 will be negative, and hence the integrator output voltage at 66, and the magnitude of the negative voltage at inverter output node 74 and the magnitude of the correction current through resistor 80 will continue to grow. However, when the magnitude of the correction current is equal to the magnitude of the dark current from diode 20, there will be no net current flow into preamplification means input node 38. Accordingly, the voltage at preamplification means output node 40 and hence at integrator input node 60, will go to zero or ground potential. The integrator output voltage at node 66 will then stabilize and remain unchanged, as will the negative voltage at node 74 and hence the correction current through resistor 80. Thus, the system reaches equilibrium when the correction current through resistor 80 equals the dark current from diode 20. The component values are selected so that the system comes substantially to equilibrium before the end of the dark interval.

Before the end of the dark interval, but after the correction current has substantially reached equilibrium, timing unit 26 actuates switch 56 to open and hence to isolate the input node 60 of integrator 62. Once switch 56 is opened and the integrator input is isolated, the integrator output remains substantially constant and the inverter output and correction current through resistor 80 likewise remain substantially constant. This condition prevails until the next dark interval, whereupon timing unit 26 closes switch 56 once again and the same cycle of operations is repeated to reset the correction current. Therefore, between dark intervals, the system applies a correction current throught resistor 80 substantially equal in magnitude but opposite in sense to the photodetector output current prevailing during the immediately preceding dark interval.

Between the dark intervals, timing unit 26 actuates the LED drives and hence LED's 16 and 18 to emit alternating bursts of red and infrared light. Some of the light from the LED's will be transmitted through the patient's body structure or fingertip 14 to photodiode 20. Thus, the signal from photodiode 20 during each burst of light will include both a component due to ambient light and a component caused by the light transmitted through the patient's body structure from one of the LED's. Assuming that the amount of ambient light impinging on the photodiode changes slowly, the amount of ambient light impinging on the photodiode will be substantially constant during the relatively brief period between dark intervals. Therefore, the ambient light component of the photodetector output signal at any time during the period between dark intervals will be substantially equal to the ambient light component prevailing during the preceding dark interval and hence will be equal in magnitude but opposite in sense to the correction current applied through resistor 80. The correction current will substantially cancel the component of the photodiode current caused by ambient light. The net current into preamplifier input node 38 will be substantially equal to the signal component caused by light transmitted from the LED's. The preamplifier output voltage at node 40 thus will be substantially representative of only the signal component, and hence will represent only the light transmitted through the body from whichever LED is illuminated.

Timing means 26 actuates switch 46 to direct the output voltage or signal from preamplifier output node 40 to the appropriate signal processing channel, viz., to red signal processing channel 48 while red LED 16 is illuminated, and to IR signal processing channel 50 while IR LED 18 is illuminated. Each signal processing channel thus receives a succession of signal samples representing the light transmitted through the patient's body structure at the associated wavelength, and hence representing the transmissivity of the body structure at the particular wavelength. In red signal processing channel 40 the successive signal samples are smoothed into a substantially continuous signal by the first low pass filter in that channel. This continuous signal represents a plot of red light transmissivity of the body structure versus time. Values representing that signal are fed by one analog to digital converter into microprocessor 52. As the AC or varying component of the red transmissivity signal typically will be small compared to the DC component, each such value will represent a good approximation of the DC value. Further, microprocessor 52 performs a digital low pass filtering to recover a more accurate DC value from successive digital values. The signal from the first low pass filter within red signal processing channel 48 is also fed through the high pass filter in that channel. The high pass filter strips out the DC component, leaving the AC component which is then amplified and again low pass filtered to remove residual switching frequency components and the like. This amplified AC signal is then successively sampled by the sample and hold device within channel 48 operating under the control of microprocessor 52. Successive sampled values are fed through a further analog to digital coverter within channel 48 into the microprocessor, and the microprocessor 52 determines the AC or peak to peak values of the red transmissivity signal from these successive values. Infrared signal processing channel 50 coacts with microprocessor 52 in substantially the same way to recover AC and DC components of the infrared transmissivity signal. From these transmissivity signals, microprocessor 52 calculates the level of oxygen or "oxygen saturation" in the patient's blood and displays that result on display unit 54. The oxygen level in the patient's blood can be calculated according to the formulas:

Oxygen Saturation = $AR^2 + BR + C$

WHERE:

$$R = \frac{(AC_R/AC_{IR})}{(DC_R/DC_{IR})}$$

$AC_R$ and $DC_R$ are the AC and DC components, respectively, of the red transmissivity signal;

$AC_{IR}$ and $DC_{IR}$ are the AC and DC components respectively of the infrared transmissivity signal; and A, B and C are constants determined by empirical curve fitting in design of the system, against the results of standard blood oxygen determinations.

As the transmissivities of the body structure change with the patient's pulse, the system should be switched between red and infrared light at a switching frequency greater than the pulse frequency. Typically, a switching frequency of about 300 Hz is employed. The dark intervals typically are interspersed with the alternating bursts of red and infrared light so that a dark interval follows after each burst or so that a dark interval follows after every other burst. In the first arrangement, the sequence of a red burst, a dark interval, an infrared burst and a further dark interval would constitute one switching cycle, and this switching cycle is repeated at the switching frequency, viz., typically about once every 1/300th second. In the second arrangement, the sequence of a red light burst, an infrared light burst and a single dark interval is repeated once on each switching cycle. With dark intervals provided at rates comparable to the switching frequency, changes in ambient light and hence changes in the ambient light component of the photodiode current or signal between dark intervals caused by factors such as movement of the patient or of the probe 10 will be insignificant. Where the ambient lighting includes significant flicker components, typically at about twice the line frequency or about 100–120 Hz, these flicker components may induce appreciable ambient light changes between dark intervals. These changes in ambient light will induce corresponding changes in photodetector output signal or current between dark intervals. Inasmuch as the correction current applied through resistor 80 will not change between dark intervals, the system does not compensate for these flicker or other rapidly varying components, and hence these components will be reflected in the amplified signal appearing at preamplifier output node 40. However, as in conventional systems, these flicker components are effectively blocked by low pass filters included in the signal processing channels. Stated another way, any variation in ambient light at a frequency comparable to the pulse frequency will be slow enough that the change between dark intervals is essentially insignificant. Changes at frequencies comparable to the pulse frequency will be effectively tracked by corresponding changes in the correction current during successive dark intervals. Components of the ambient light changing at frequencies comparable to the pulse frequency will thus be effectively counteracted by the correction current and hence will be eliminated by the preamplifier output signal. Components at higher frequencies, such as the aforementioned flicker frequency components, will be reflected in the preamplifier output signal, but these can be segregated from the useful signals by low pass filtering and hence are not particularly serious.

As will be appreciated, integrator 62 and inverter 68 and resister 80 cooperatively define a servo feedback loop which effectively holds the ambient light component or offset the inputs applied to the preamplifier means input node 38 to zero. Numerous advantages arise from this approach as compared to prior art systems using a switched capacitor in the preamplifier output to provide a ground referenced signal. The capacitor 68 utilized in the preferred system discussed above can be far smaller than a capacitor required in a comparable system according to the prior art. This significantly reduces the capacitive load on the operational amplifier 36 in preamplification means 34, and therefore facilitates stable operation of operational amplifier 36.

Operational amplifier 36 is more effectively protected from overloading caused by ambient light components in the photodetector output signal. As compared with a prior art system utilizing a preamplification feedback resistor of the same value and hence having the same gain, the ability of the system to withstand ambient light without overloading is increased by a ratio of $R_{44}/R_{80}$, where $R_{44}$ is the value of resistor 44 and $R_{80}$ is the value of resistor 80. Alternately, the value $R_{44}$ of the feedback resistor in a system according to the present invention, and hence the gain of preamplification means 34 can be many times greater than the comparable resistor value used in a system according to the prior art, while still maintaining the same ability to withstand overloading caused by ambient light. Typically, systems according to the present invention provide a combination of increased gain and increased resistance to ambient light overloads. The currents flowing through switch 56 typically are smaller than the currents flowing in the switch used in the outputcapacitor system of the prior art. Resistor 58 is in series with switch 56, and the value of resistor 58 typically is large in comparison to the resistance of switch 56. Thus, variations in the resistance of switch 58 will have relatively little effect on the response time of integrator 62.

Figure 2:
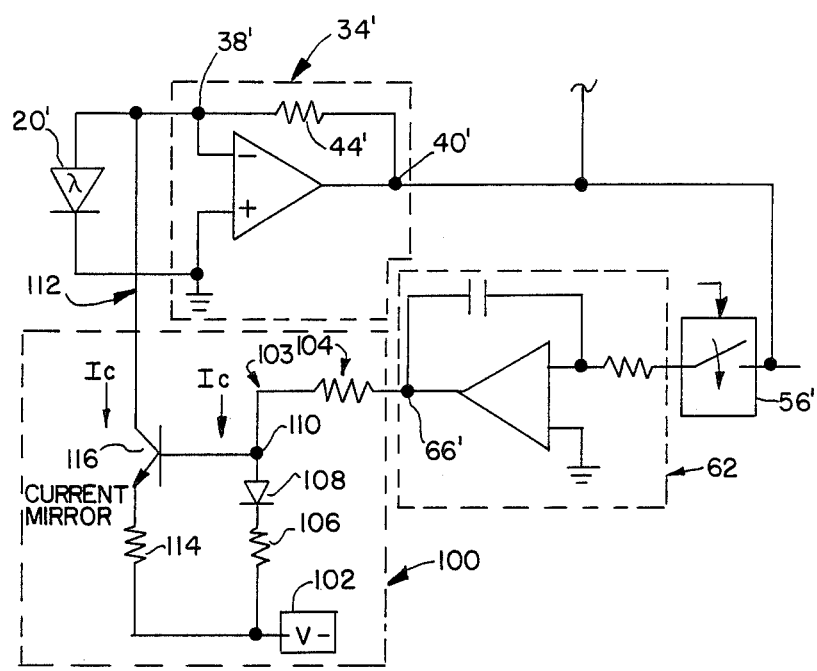
FIG. 2 is a fragmentary schematic diagram showing a portion of apparatus according to a further embodiment of the invention.

Apparatus according to a further embodiment of the present invention is shown in FIG. 2. This apparatus includes a photodiode 20', preamplification means 34', integrator switch 56' and integrator 62' substantially the same as those described above with reference to FIG. 1. However, in place of the inverter 68 and correction current resistor 80 utilized in the embodiment of FIG. 1, the apparatus according to FIG. 2 employs a so-called "current mirror" device 100. The current mirror device includes a source 102 for negative bias voltage and a circuit 103 incorporating two resistors 104 and 106 connected in series, with a diode 108 therebetween. The circuit 103 is connected between the output node 66' of integrator 62 and negative bias voltage source 102. The circuit 103 defines a node 110 between the two resistors. A correction current circuit branch 112 extends from the input node 38' of preamplification means 34' to negative voltage source 102. A fixed resistor 114 is connected in branch 112, as are the collector and emitter of a transistor 116. The base of transistor 116 is connected to node 110 of circuit 103. As will be appreciated, the impedance across the collector and emitter of transistor 116 and hence the impedance between node 38' and negative voltage source 102 will vary with the voltage at node 110. Therefore, the magnitude of correction current flowing through circuit branch 112 will vary with the magnitude of the accumulated signal or voltage at the integrator output node 66'.

Apparatus according to this embodiment of the present invention operates similarly to the apparatus described above with reference to FIG. 1. Here again, during each dark interval, the photodetector output current from photodetector 20' causes the preamplifier output voltage at node at 40' to go negative, and hence causes a progressively increasing positive voltage to appear at integrator output node 66'. This in turn causes an increasing current through resistors 104 and 106, and hence an increase in voltage at node 110, leading to a corresponding decrease in the impedance across the collector and emitter of transistor 116 and hence a corresponding increase in the correction current on branch 112. This continues until the correction current equals the photodiode output current or dark current prevailing during the dark interval and the system comes to equilibrium. After the dark interval, switch 56' opens. The value of the integrator output voltage at node 66' and hence the correction current on branch 112, remain substantially constant until the next dark interval. Changes in the impedance of diode 108 with temperature counteract changes in the characteristics of transistor 116 with temperature. In other respects, the system operates in generally the same way as that discussed above with reference to FIG. 1.

As will be appreciated, numerous variations and combinations of the features described above can be utilized without departing from the present invention as defined in the claims. For example, the photodiode 20 or 20' may be reverse-biased, as by a bias voltage source connected between the photodiode and ground. Also, photodetectors other than photodiodes may be used. The feedback loop may be arranged without an integrator. In one such arrangement, the amplified signal during a dark interval can be passed to the microprocessor via an analog to digital converter. The microprocessor may record the value of this signal during the dark interval and provide this value continually until the next dark interval to the control input of the correction current device. The microprocessor would be linked to the timing means to coordinate this action. Also, where the only parameter of the blood to be monitored is a pulse parameter, only one signal processing channel is required, and only one light wavelength is employed. The microprocessor may also perform other, conventional functions such as controlling the gain of the amplifiers in the signal processing channels and the power applied to the LED drives to keep the signals supplied to the various analog to digital converters in range. As these and other variations and combinations can be employed, the foregoing description of the preferred embodiments should be taken by way of illustration rather than by way of limitation of the present invention as defined by the claims.

I claim:

1. Apparatus for monitoring a parameter of the blood in a body structure comprising:
    (a) photodetector means for producing a photodetector output signal related to the amount of light impinging upon said photodetector means;
    (b) preamplification means having an input node for providing an amplified signal related to a signal supplied to said input node, said input node being connected to to said photodetector means for receipt of said photodetector output signal;
    (c) illumination means for emitting light and directing the emitted light through the body structure so that emitted light transmitted through said body structure will impinge upon said photodetector means;
    (d) means for periodically interrupting operation of said illumination means to provide dark intervals, whereby the photodetector output signal during each said dark interval will be a dark interval photodetector output indicative of ambient light impinging on said photodetector means;
    (e) correction means for applying to said input node of said preamplification means a correction signal substantially equal in magnitude but opposite in sense to the dark interval photodetector output signal whereby said amplified signal will be substantially corrected for the effects of ambient light on said photodetector means; and
    (f) interpretation means for determining said parameter of the blood from said corrected, amplified signal.

2. Apparatus as claimed in claim 1 wherein said correction means includes means for determining the photodetector output signal prevailing during each said dark interval by monitoring said amplified signal.

3. Apparatus as claimed in claim 2 wherein said correction means includes feedback means for adjusting said correction signal during each dark interval so as to bring said amplified signal substantially to a predetermined null value and then maintaining said correction signal as so adjusted until the next dark interval.

4. Apparatus as claimed in claim 3 wherein said feedback means includes means for integrating said amplified signal during each said dark interval and means for providing said correction signal during each period between dark intervals responsive to the integrated amplified signal accumulated during the last previous dark interval.

5. Apparatus as claimed in claim 1, wherein said photodetector means includes means for providing said photodetector output signal as a photodetector current such that the magnitude of said photodetector current is directly related to the amount of light impinging upon said photodetector means, said correction means including means for applying said correction signal as a current substantially equal but opposite to the photodetector current prevailing during the last preceding dark interval.

6. Apparatus as claimed in claim 5 wherein said preamplifier means includes a transresistance amplifier stage incorporating an operational amplifier defining said input node, an output node and a feedback resistor connected between said input and output nodes.

7. Apparatus as claimed in claim 6 wherein said correction means includes integrator means having an input and an output for integrating a signal applied to said integrator input and providing an integrator output voltage proportional to said integrated signal, integrator switching means for connecting said integrator input to said output node of said preamplification means only during said dark intervals, and current generator means for generating said correction current in response to said integrator output voltage.

8. Apparatus as claimed in claim 6 wherein said current generator means includes an inverter operational amplifier having inverter input and output nodes, an inverter feedback resistor connected across said inverter input and output nodes, an inverter input resistor connected between said inverter input node and said integrator output node, and a proportioning resistor connected between said inverter output node and said input node of said preamplification means.

9. Apparatus as claimed in claim 7 wherein said current generator means includes a correction current circuit branch connected between said input node of said preamplification means and a source of a predetermined bias voltage, and means for providing an impedance in said correction current circuit branch such that said impedance depends upon said integrator output voltage.

10. Apparatus as claimed in claim 9 wherein said current generator means includes a pair of resistors connected in series between said integrator output node and a source of predetermined bias voltage, said resistances defining therebetween a circuit node, said means for providing an impedance being responsive to the voltage at said circuit node.

11. Apparatus as claimed in claim 10 wherein said means for providing an impedance includes a transistor having a control input connected to said circuit node.

12. Apparatus as claimed in claim 7 wherein said means for periodically interrupting operation of said illumination means includes a timing means and wherein said integrator switching means is connected to said timing means and responsive thereto.

13. Apparatus as claimed in claim 1 wherein said illumination means includes means for emitting light at a plurality of wavelengths, the apparatus further includes sequence control means for controlling said illumination means to emit light of different wavelengths in alternating sequence at times other than said dark intervals, and wherein said interpretation means includes means for sampling said corrected, amplified signal in sequence correlated with said alternating sequence of wavelengths and interpreting different samples of said amplified signal as representing transmissivity of the body structure at different wavelengths.

14. A method of monitoring a parameter of the blood in a body structure comprising the steps of:
  (a) producing a photodetector output signal related to the amount of light impinging upon a photodetector means and providing said photodetector output signal to an input of a preamplifier;
  (b) amplifying the signal applied to said input of said preamplifier so as to provide an amplified signal;
  (c) illuminating the body structure by emitting light and directing the emitted light through the body structure so that emitted light transmitted through said body structure impinges upon said photodetector;
  (d) periodically interrupting said illuminating step to provide dark intervals, whereby the photodetector output signal during each said dark interval will be a dark interval photodetector output indicative of ambient light impinging on said photodetector means; and
  (e) subtracting a correction signal from said photodetector output signal before said photodetector output signal is amplified in step (b), the magnitude of said correction signal being substantially equal to the magnitude of said dark interval photodetector output signal, whereby said amplified signal will be substantially corrected for the effect of ambient light; and
  (f) determining said parameter of the blood from said corrected amplified signal.

* * * * *